US010544442B2

(12) United States Patent
Formolo et al.

(10) Patent No.: US 10,544,442 B2
(45) Date of Patent: Jan. 28, 2020

(54) METHODS FOR THE DETERMINATION OF BIOGENIC GAS

(71) Applicant: ExxonMobil Upstream Research Company, Spring, TX (US)

(72) Inventors: Michael J. Formolo, The Woodlands, TX (US); Isolde Belien, Kingwood, TX (US); Aaron B. Regberg, Houston, TX (US)

(73) Assignee: ExxonMobil Upstream Research Company, Spring, TX (US)

( * ) Notice: Subject to any disclaimer, the term of this patent is extended or adjusted under 35 U.S.C. 154(b) by 316 days.

(21) Appl. No.: 15/367,906

(22) Filed: Dec. 2, 2016

(65) Prior Publication Data

US 2017/0166947 A1 Jun. 15, 2017

Related U.S. Application Data

(60) Provisional application No. 62/267,592, filed on Dec. 15, 2015.

(51) Int. Cl.
| | |
|---|---|
| *G01N 33/48* | (2006.01) |
| *G01N 33/50* | (2006.01) |
| *C12Q 1/02* | (2006.01) |
| *G01N 33/24* | (2006.01) |
| *G01N 33/00* | (2006.01) |

(52) U.S. Cl.
CPC ............ *C12Q 1/02* (2013.01); *G01N 33/004* (2013.01); *G01N 33/005* (2013.01); *G01N 33/241* (2013.01)

(58) Field of Classification Search
None
See application file for complete search history.

(56) References Cited

U.S. PATENT DOCUMENTS

| | | | |
|---|---|---|---|
| 7,571,644 B2 | 8/2009 | Ibrahim et al. | |
| 8,355,872 B2 | 1/2013 | Rowan | |
| 2005/0142113 A1* | 6/2005 | McLeod | A61K 39/002 424/93.2 |
| 2008/0152967 A1* | 6/2008 | Roychowdhury | C02F 11/04 429/422 |
| 2009/0130732 A1 | 5/2009 | Fedorak et al. | |
| 2009/0130734 A1* | 5/2009 | Mets | C12M 21/04 435/167 |
| 2010/0155078 A1 | 6/2010 | Walters et al. | |

(Continued)

OTHER PUBLICATIONS

Cumulative frequency. In Helicon (Ed.), The Hutchinson unabridged encyclopedia with atlas and weather guide. Abington, UK: Helicon. Retrieved from www.credoreference.com on Jan. 28, 2019. (Year: 2018).*

(Continued)

*Primary Examiner* — Russell S Negin
(74) *Attorney, Agent, or Firm* — ExxonMobil Upstream Research Company—Law Department

(57) ABSTRACT

Provided are methods of estimating a volume of a biogenic gas for an area of interest. The method includes predicting a methanogenesis rate for one or more of the periods of time for the area of interest based on energy available for microbial activity and calculating the volume of the biogenic gas based on the predicted methanogenesis rate for the one or more of the periods of time for the area of interest.

13 Claims, 5 Drawing Sheets

(56) References Cited

U.S. PATENT DOCUMENTS

| | | |
|---|---|---|
| 2011/0308790 A1 | 12/2011 | Strapoc et al. |
| 2012/0036923 A1 | 2/2012 | Valentine |
| 2012/0309098 A1 | 12/2012 | Behar et al. |
| 2014/0163883 A1 | 6/2014 | Granjeon et al. |
| 2015/0038348 A1 | 2/2015 | Ashby et al. |
| 2015/0066461 A1 | 3/2015 | Kacewicz |
| 2015/0104795 A1 | 4/2015 | Pfeiffer et al. |

OTHER PUBLICATIONS

Kawaguchi, H. et al., "Methane production by *Methanothermobacter thermautotrophicus* to recover energy from carbon dioxide sequestered in geological reservoirs", *Journal of Bioscience and Bioengineering*, Elsevier, Amsterdam, NL, vol. 110, No. 1, Jan. 27, 2010, pp. 106-108 (XP027086404).

Clayton, C., (1992) "Source volumetrics of biogenic gas generation" In: Vially, R., (ed.) Bacterial Gas. Editions Technip: Paris, pp. 191-204.

Katz, B. J., (1995) "Biogenic Gas—Its Formation and Economic Significance", Proceedings Indonesian Petroleum Association, 24th Annual Convention, Oct. 1995, IPA 95-1.3-222; p. 461-474.

Katz, B.J. (2011) "Microbial Processes and Natural Gas Accumulations", *The Open Geology Journal*, vol. 5, pp. 75-83.

Nmegbu, C. et al (2014) "Modeling the Kinetics of Biogenic Gas Production During Microbial Enhanced Oil Recovery," *International Journal of Scientific and Engineering Research*, vol. 5, Issue 6, Jun. 2014, pp. 332-336.

Wallman, K., et al. (2006) "Kinetics of organic matter degradation, microbial methane generation, and gas hydrate formation in anoxic marine sediments". Geochimica et Cosmochimica Acta, 70, pp. 3905-3927.

Bryant et al. (1989) "Review of Microbial Technology for Improving Oil Recovery", *SPE Reservoir Engineering*, pp. 151-154.

Li et al. (2014) "Microbial Abundance and Community Composition Influence Production Performance in a Low-Temperature Petroleum Reservoir", *Environmental Science and Technology*, vol. 48, pp. 5336-5344.

Ozgul (2002), "Geochemical Assessment of Gaseous Hydrocarbons: Mixing of Bacterial and Thermogenic Methane in the Deep Subsurface Petroleum System, Gulf of Mexico Continental Slope", *Thesis in partial fulfillment of the requirements for the degree of Master of Science at Texas A&M University*, pp. 1-167.

Stolper et al. (2014) "Formation temperatures of thermogenic and biogenic methane", *Science*, vol. 344, Issue 6191, pp. 1500-1503.

Stolper et al. (2015) "Distinguishing and understanding thermogenic and biogenic sources of methane using multiply substituted isotopologues", *Geochimica et Cosmochimcia Acta*, vol. 161, pp. 219-247.

Waldron et al. (2007) "Salinity Constraints on Subsurface and Archael Diversity and Methanogensis in Sedimentary Rock Rich in Organic Matter", *Applied and Environmental Micorbiology*, vol. 73, No. 13, pp. 4171-4179.

\* cited by examiner

METHODS FOR THE DETERMINATION OF BIOGENIC GAS

CROSS REFERENCE TO RELATED APPLICATION

This application claims the benefit of U.S. Provisional Application No. 62/267,592 filed Dec. 15, 2015, the entirety of which is incorporated by reference herein.

FIELD OF THE INVENTION

The present application provides techniques and methods for the estimation of a volume of biogenic gas which may be used to enhance hydrocarbon recovery.

BACKGROUND OF THE INVENTION

Microbial or biogenic gas is typically generated in anaerobic, sulfate-free sediments at low temperatures (usually less than 75° C.) by a community of microbes that include fermentative bacteria, acetogenic bacteria, and a group of Archaea called methanogens. Methanogens can produce methane by either carbon dioxide reduction ($CO_2$+ $4H_2 \rightarrow CH_4 + 2H_2O$) or acetate fermentation ($CH_3COOH \rightarrow CH_4 + CO_2$) with the former pathway being far more common in marine settings and the latter more common in fresh water settings. Although microbial methane is ubiquitous in marine and fresh water sediments, economically recoverable accumulations of microbial gas are less common than thermogenic gas accumulations and require a combination of favorable geological and biological conditions.

Biogenic gas systems, specifically the gas generation mechanisms, differ in many aspects from thermogenic hydrocarbon systems. For example, the timing of microbial gas generation is not controlled by the burial history and thermal cracking kinetics of kerogen but by the timing of the development of optimal living conditions (temperature, nutrient, and pore water chemistry) of methanogens. Early stage methanogenesis (also called primary methanogenesis) begins soon after deposition of sediments, and late-stage methanogenesis (also called secondary methanogenesis) occurs later in geologic time in sedimentary rocks inoculated with methanogens and nutrients by meteoric groundwater. Because of the differences between biogenic gas systems and thermogenic hydrocarbon systems, the approaches for assessing generated hydrocarbon volumes need to be process specific for biogenic and thermogenic systems. Therefore, models specific to biogenic hydrocarbon volume generation need to capture the complexity of biological systems while also accounting for geological conditions. That is, models should adhere to biological and geochemical conditions that determine the feasibility of the microorganisms to produce biogenic gas, and thus should account for microbial kinetic reactions and thermodynamic conditions that provide available free energy. These conditions include temperature, pressure, the concentrations of reactants, such as $CO_2$ and $H_2$, and concentrations of products, such as $CH_4$.

Previous approaches to modeling biogenic gas production have used the total organic carbon or volume of the biogenic gas producing region. Such models directly convert organic matter, both in its bulk organic carbon concentration and in compositional stoichiometric quantities, and, therefore, are not constrained by kinetics or thermodynamics. As such, these organic-matter driven models often fail to accurately predict the volumes of biogenically produced gas as they do not integrate any microbiological component.

Examples of two existing models are those proposed by Clayton (1992) and the kinetics of organic matter degradation published by Wallman et al. (2006). See Clayton, C., (1992) Source volumetrics of biogenic gas generation. In: Vially, R., (ed.) Bacterial Gas. Editions Technip: Paris, pp. 191-204; and Wallman, K., Aloisi, G., Haeckel, M., Obzhirov, A., Pavlova, G., and Tischchenko, P. (2006) Kinetics of organic matter degradation, microbial methane generation, and gas hydrate formation in anoxic marine sediments. Geochimica et Cosmochimica Acta, 70, pp. 3905-3927. The Clayton (1992) approach integrates the drainage or fetch area, which is a geometric area that can produce a hydrocarbon, and the bulk total organic carbon pool to predict a volume of biogenic gas. The Clayton model uses a factor of 10% of the total available organic carbon to calculate the generated volume of biogenic gas regardless of the geochemical conditions in the fetch area which may impact microbial activity. The general characterization of 10% transformation of organic carbon to methane assumes that microbial generation is constant everywhere which is not likely given that geochemical conditions are variable in different environments. These differences could be the presence of products and reactants or temperature, all of which change the kinetics and thermodynamics of microbial methanogenesis. As such, the Clayton model often fails to accurately predict the volume of biogenic gas that has been generated.

The Wallman et al. (2006) model is driven by the overall degradation of organic matter in marine sediments. This approach focuses on the microbial activity at shallow sediment depths in these environments and not necessarily in the deeper depths of the sediments where the temporally protracted generation of biogenic methane is important for the generation of commercially viable volumes of biogenic gas. Accordingly, the model of Wallman et al. (2006) may not be directly transferable to deeper biogenic gas producing areas. In addition, the model of Wallman et al. (2006) requires data that is not often available in exploration settings, such as data detailing the pore-water chemistry sampled at high-resolution over great depths, and dissolved concentrations of $CH_4$, $SO_4^{2-}$, and $H_2$, as well as other inorganic parameters. As such, the Wallman et al. (2006) model often fails to accurately predict the volume of biogenic gas that has been generated.

Therefore, the majority of existing models suffer from deficiencies in that they do not integrate the known environmental conditions with microbial activity and energy requirements over geologic timescales. The absence of these parameters limits the ability of these models to predict biogenic gas generation over geological timescales. Therefore, there remains a need for the ability to accurately predict the volume of generated biogenic gas, which is important in assessing and exploring biogenic hydrocarbon systems. An exemplary embodiment of the present invention will more accurately model the conditions responsible for methanogenesis over geological timescales.

Background references may include: Chukwuma Nmegbu, "Modeling the Kinetics of Biogenic Gas Production During Microbial Enhanced Oil Recovery," *International Journal of Scientific and Engineering Research*, Vol. 5, Issue 6, June 2014; Barry J. Katz, "Biogenic Gas—Its Formation and Economic Significance", *Proceedings Indonesian Petroleum Association, 24th Annual Convention*, October 1995, IPA 95-1.3-222; Barry J. Katz, "Microbial Processes and Natural Gas Accumulations". The Open Geology Journal, Vol. 5, pp. 75-83 (2011); and U.S. Patent Application Publication Nos. 2010/0155078, 2011/0308790, 2012/0309098, 2014/0163883, 2015/0066461, and 2015/0104795.

SUMMARY OF THE INVENTION

Described herein are methods and techniques for the estimation of a volume of biogenic gas which may be used to enhance hydrocarbon recovery.

The method may comprise identifying a plurality of environmental characteristics for one or more periods of time for an area of interest. The environmental characteristics may comprise, a hydrogen concentration, a carbon dioxide concentration, a methane concentration, pore-water chemistry (e.g., sodium concentration, chloride concentration, bicarbonate concentration, or pore-water pH), and combinations thereof. In some embodiments, one or more of the environmental characteristics are identified by analyzing a sample from the area of interest and measuring the characteristic by chemical analysis. In some embodiments, one or more of the environmental characteristics are determined by averaging previously determined values.

A methanogenesis rate may be determined by utilizing the environmental characteristics and integrating a function indicating the hydrogen activity for the period of time in the area of interest, a function indicating the carbon dioxide activity for the period of time in the area of interest, and a function indicating the microbial respiration energy ($R_e$) for the period of time in the area of interest.

The volume of biogenic gas for the one or more periods of time for the area of interest may then be determined from the methanogenesis rate. In some embodiments, volumes may be predicted for two or more periods of time and a comparison may be made between the time periods. In some embodiments, volumes may be predicted at two or more different temperatures and a comparison may be made between the volume produced at a first temperature and the volume produced at a second temperature.

In some embodiments the area of interest may be an oil and/or gas field. In some embodiments, the area of interest may be a deep-water oil and/or gas field. In some embodiments, the method may further comprise, extracting hydrocarbons from the oil and/or gas field.

BRIEF DESCRIPTION OF THE FIGURES

The foregoing and other advantages of the present disclosure may become apparent upon reviewing the following detailed description and drawings of non-limiting examples of embodiments.

DETAILED DESCRIPTION OF THE INVENTION

Figure 1:
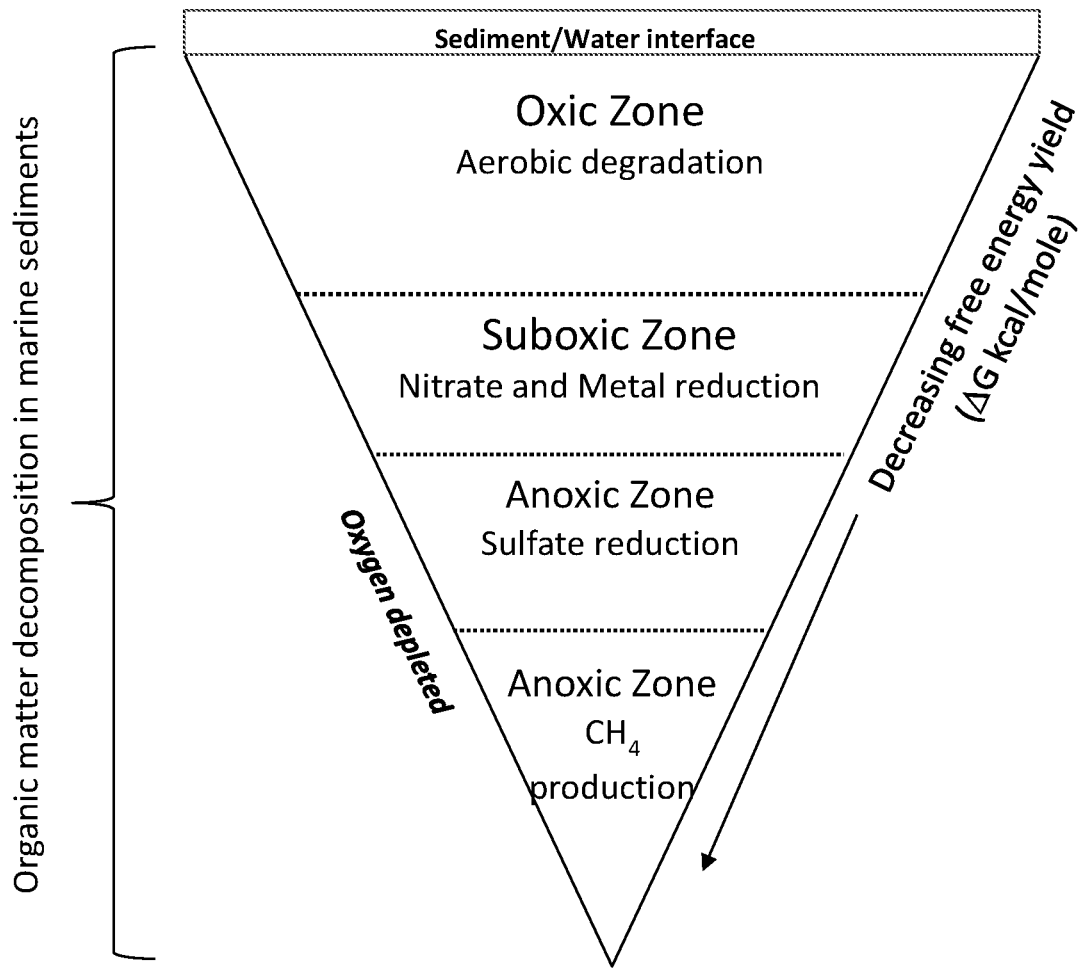
FIG. 1 is a diagram of the hierarchy of microbial processes degrading organic matter with increasing sediment and burial depth in marine environments. The change in the relative free energies yielded of various decomposition, or cellular respiration processes, is also illustrated.

While for purposes of simplicity of explanation, the illustrated methodologies are shown and described as a series of blocks, it is to be appreciated that the methodologies are not limited by the order of the blocks, as some blocks can occur in different orders and/or concurrently with other blocks from that shown and described. Moreover, fewer than all the illustrated blocks may be required to implement an example methodology. Blocks may be combined or separated into multiple components. Furthermore, additional and/or alternative methodologies can employ additional, not illustrated blocks. While the figures illustrate various serially occurring actions, it is to be appreciated that various actions could occur concurrently, substantially in parallel, and/or at substantially different points in time.

Persons skilled in the technical field will readily recognize that in practical applications of the disclosed methodology, it is partially performed on a computer, typically a suitably programmed digital computer. Further, some portions of the detailed descriptions which follow are presented in terms of procedures, steps, logic blocks, processing and other symbolic representations of operations on data bits within a computer memory. These descriptions and representations are the means used by those skilled in the data processing arts to most effectively convey the substance of their work to others skilled in the art. In the present application, a procedure, step, logic block, process, or the like, is conceived to be a self-consistent sequence of steps or instructions leading to a desired result. The steps are those requiring physical manipulations of physical quantities. Usually, although not necessarily, these quantities take the form of electrical or magnetic signals capable of being stored, transferred, combined, compared, and otherwise manipulated in a computer system.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present application, discussions utilizing the terms such as "processing" or "computing", "calculating", "determining", "displaying", "copying," "producing," "storing," "adding," "applying," "executing," "maintaining," "updating," "creating," "constructing" "generating" or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

As used herein, "concurrently" means happening, performing or occurring at time periods that overlap or are within a time interval with respect to each other. For example, if a first operation is being performed during a first time period and a second operation is being performed during a second time period, the operations are performed concurrently with respect to each other if the first time period and second time period overlap or the first time period and the second time period are performed within the same time interval (e.g., within the same stage of a process).

As mentioned earlier, biogenic gas is produced as part of the sequential decomposition of sedimentary organic matter or hydrocarbons. Methanogens are anaerobes that are active when oxygen is absent. Referring to FIG. 1, the transition from oxic to suboxic to anoxic degradation processes is illustrated with the decreasing free energy yields associated with microbial metabolism. As the free energy of these processes can vary under different environmental conditions, the absolute values of the free energy, i.e., ΔG in kcal/mole, may also vary and thus are not provided in FIG. 1. As shown in FIG. 1, aerobic respiration is the most efficient process, followed by nitrate and metal reduction, followed by sulfate reduction, and then methanogenesis. The position of methanogenesis in the anaerobic decomposition or remineralization sequence is largely the result of the relative efficiencies in deriving energy from the available substrate. Under suboxic and anoxic conditions the denitrifiers and metal reducers, which are more efficient in extracting energy, dominate over sulfate reducers, which dominate over methanogens. Consequently, methanogenesis does not effectively begin in marine systems until pore-water sulfate has been significantly reduced and sulfate reducers are no longer active. The depth at which this transition occurs is controlled by the availability of sulfate, the burial rate, and the nature of the organic matter. The depth to the onset of methanogenesis is greatest when the organic matter is more refractory and the rates of sedimentation are slow. In marine systems, sulfate reduction may persist to depths of several hundred meters. However, the general absence of sulfate in nonmarine systems can permit methanogenesis to begin at much shallower depths.

Methanogens do not directly decompose available organic matter but metabolize decomposition products of earlier bacterial mediated reactions. Two primary pathways have been identified for methanogenesis: acetate fermentation, $CH_3COOH \rightarrow CH_4+CO_2$ and $CO_2$ reduction, $CO_2+4H_2 \rightarrow CH_4+2H_2O$.

Methanogenic activity is strongly influenced by temperature. Although methanogens can survive over a wide temperature range of approximately 0 to 100° C., the optimum temperature for methanogenic bacterial activity of interest to the petroleum industry is typically between 20° C. and 50° C., or between 30° C. and 40° C. The group of methanogens which display a lower temperature for optimum metabolic activity would commonly be in competition with sulfate reducers and once established would, under most circumstances, produce gas prior to seal development. The thermophilic forms would produce most of their hydrocarbons coincident with thermogenic gas generation with their products being indistinguishable from those of thermal cracking.

A typical methanogenesis curve suggests that as much as one third of the potential biogenic methane yield occurs at temperatures below 30° C., another third takes place at a temperature in the range of from 30° C. to 40° C., and that the remaining third of the biogenic gas is produced at a temperature between 40° C. and 70° C. Variations in sedimentation rate, porewater chemistry, nutrients and/or geothermal gradient through time would alter the shape of the cumulative generation curve.

Previous attempts to model the generation of biogenic gas utilize the concentration of organic carbon or the composition of the organic matter as the threshold to determine the biogenic generative capacity of sediments. However, methanogens are sensitive to the availability of hydrogen and volume of generated methane in the environment. The concentration of hydrogen is also a critical component to determine which microbial community is active. For example, changes in the hydrogen concentration may allow other microbial communities to become established, such as sulfate reducers, which would suppress methanogenic activity. Under the proper geochemical conditions, including adequate $H_2$ concentrations, methanogens will generate methane. Inputting these known conditions into a geochemical model that utilizes geochemical boundary conditions determined from analyzed pore water and under thermodynamically feasible conditions provides an improved framework to assess the volume of biogenic gas generated in an area of interest.

Figure 2:
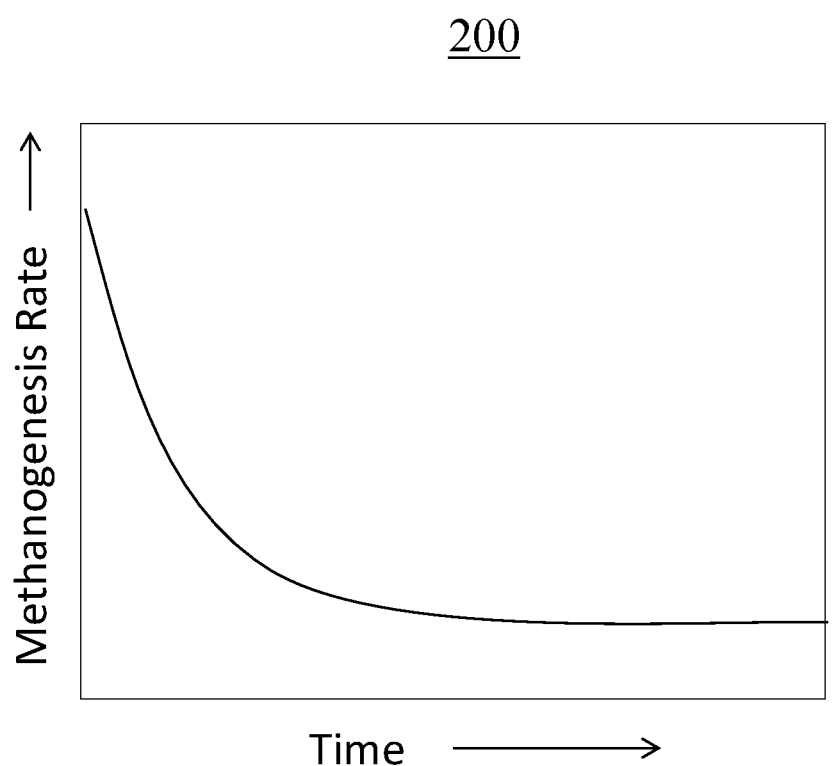
FIG. 2 is an exemplary diagram of a methanogenesis curve as a function of time.

Illustrated in FIG. 2 is an example of a hypothetical, qualitative methanogenesis curve 200 as a function of time. The x-axis of FIG. 2 illustrates time which may be in years while the y-axis illustrates the methanogenesis reaction rate which may be in $nmol/cm^3/yr$. Thus, as seen in FIG. 2 the methanogenesis rate decreases and approaches a steady-state over time as thermodynamic changes in the geochemical surroundings occur.

The methods described herein integrate a microbial kinetic model that is constrained by the thermodynamic conditions determined by the availability of reactants, such as, $HCO_3^-$, $CO_2$, and $H_2$, and the formation of products, namely $CH_4$. Specifically, this model captures the control that the environmental geochemical and biological conditions, specifically the $H_2$ concentration, have on the free energy available to the microbial community and the ability to generate microbial methane in biogenic gas systems. Thus, constraining methane generation based upon the free-energy gain required to support the microbial activity and the $H_2$ availability allows for more accurate estimations of the volume of biogenic gas and solves some of the deficiencies of other biogenic modeling approaches such as the Clayton and Wallman models. The present methods utilize a modified dual Monod equation that includes an additional parameter, the microbial respiration function.

A Monod equation is a mathematical model for the growth of microorganisms that relates microbial growth rates in an aqueous environment to the concentration of a limiting nutrient. The Monod equation is as follows:

$$\mu = \mu_{max} \frac{S}{K_s + S}$$

where $\mu$ is the specific growth rate of the microorganisms; $\mu_{max}$ is the maximum specific growth rate of the microorganisms;
S is the concentration of the limiting substrate for growth; and
$K_s$ is the "half-velocity constant", that is, $K_s$ is the value of S when $\mu/\mu_{max}=0.5$.
$\mu_{max}$ and $K_s$ are empirical coefficients to the Monod equation that will differ between microbial species and on ambient environmental conditions. Multiple terms of the form $[S/(K_s+S)]$ may be multiplied together where more than one nutrient or growth factor has the potential to be limiting.

In this application, the methanogenesis reaction, $CO_2+4H_2 \rightarrow CH_4+2H_2O$, has a chemical donor species, $H_2$, and a chemical acceptor species, $CO_2$, and both donor and acceptor species can be limiting. Thus, the rate of the methanogenesis reaction can be modeled by modifying the Monod equation to include both the donor species and the acceptor species, forming a dual Monod equation, and by further including the additional parameter, the microbial respiration function.

The methanogenesis rate expression of an exemplary embodiment of the present methods can be expressed as follows:

Rate=$k*M*D*A*R_e$ where Rate is the methanogenesis rate;
k is a rate constant;
M is the biomass;
D is the donor function, that is D is an indication of the $H_2$ activity;
A is the acceptor function, that is A is an indication of the $CO_2$ activity; and
$R_e$ is a thermodynamic function indicating the microbial respiration energy function.

The donor function D can be as follows:

$$D = \frac{H_2}{K_D + H_2}$$

where $H_2$ is the concentration of $H_2$; and
$K_D$ is the saturation coefficient of $H_2$, that is, $K_D$ is the $H_2$ concentration at which the specific growth rate of the microbial community or organism is one-half of its maximum.

The acceptor function A can be as follows:

$$A = \frac{CO_2}{K_A + CO_2}$$

where $CO_2$ is the concentration of $CO_2$; and
$K_A$ is the saturation coefficient of $CO_2$, that is, $K_A$ is the $CO_2$ concentration at which the specific growth rate of the microbial community or organism is one-half of its maximum.

The microbial respiration energy function $R_e$ can be as follows:

$$R_e = 1 - e^{\frac{\Delta G_{redox} - m\Delta G_{atp}}{XRT}}$$

where $\Delta G_{redox} - m\Delta G_{atp}$ is the free energy change of microbial respiration;
m is the number of ATPs synthesized;
X is the average stoichiometric number of reaction;
R is the universal gas constant; and
T is the temperature.

The microbial respiration energy function $R_e$ can further be written as:

$$Re = (1 - (Q/K)^\omega) * \exp^{((-\omega * natp * \Delta Gatp)/(RT))\Omega}$$

Where Q is the reaction quotient;
K is the equilibrium constant for the reaction;
ω and Ω are reaction orders which prevent reaction from proceeding under conditions that inhibit microbial methanogenesis;
natp*ΔGatp is collectively a term that combines the number of ATP (natp) generated and the free energy required to sustain the microbial activity and generation of methane.

As described above, the microbial respiration function is the term that monitors the free energy from the reaction that is available for the organisms. The elements used to determine $R_e$ compare the free energy generated from the reaction, which is the energy available for the generation of adenosine triphosphate (ATP), at a certain set of geochemical conditions for a given time to the energy that is needed for sustained microbial activity. As long as the term $R_e$ is >0 then the reaction will proceed. This term assures that the reaction only proceeds if there is enough energy in the system to sustain metabolic activity. Thus, the term $R_e$ links the available energy determined by the thermodynamics of the environmental conditions with the kinetics of the microbial reaction generating methane.

Many models utilize the concentration of organic carbon or the composition of the organic matter as the threshold to determine the biogenic generative capacity of sediments. However, methanogens are also sensitive to the availability of hydrogen and volume of generated methane in the environment. Therefore, the concentration of hydrogen is also a critical component to determine which microbial community is active. As mentioned previously, changes in the hydrogen concentration may allow other microbial communities to become established, such as sulfate reducers, which would suppress methanogenic activity. Under the proper geochemical conditions, including adequate $H_2$ concentrations, methanogens will generate methane. Inputting these known conditions into the methods presented herein which are constrained by the geochemical conditions measured, or observed, in these environments under thermodynamically feasible conditions provides the framework to assess the volume of biogenic gas generated in an area of interest.

The kinetic portion, which is the expression for the rate of microbial methane generation, of the model is expressed by the microbial respiration function. This function incorporates how the variations in reactants and products change the thermodynamic drive and the energy available for microbial respiration as the system changes. When the thermodynamic drive approaches zero the reaction becomes less thermodynamically reasonable and will eventually terminate the kinetic portion of the model. The $R_e$ term will force the model to produce a rate equal to zero if the reaction becomes energy limiting in the sense that it cannot generate enough energy for the organisms to create ATP which is required for the organism to survive, and therefore produce biogenic gas. This provides a realistic constraint on the modeled generation volumes. This model and/or its results can also be integrated into a basin model to determine timing and volumes of gas generated in a given biogenic system.

Figure 3:
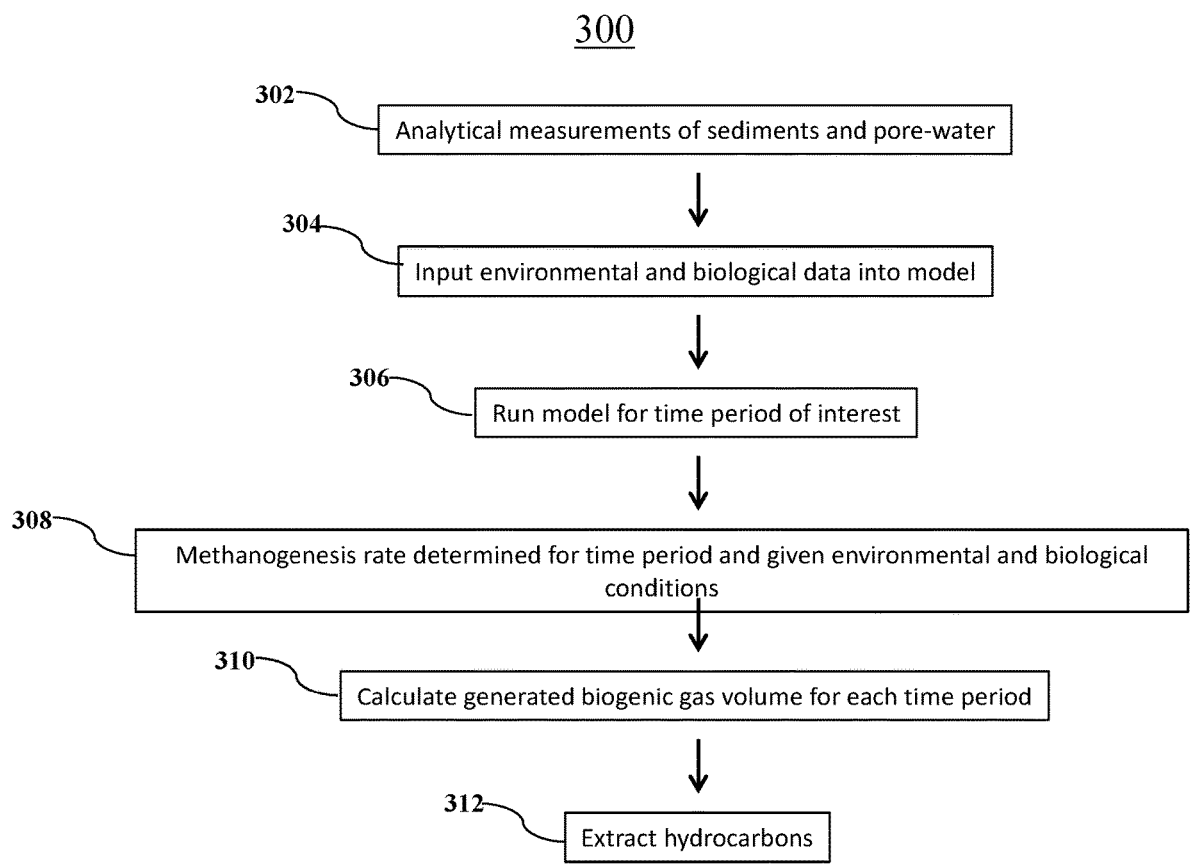
FIG. 3 is a flow diagram of an exemplary method of calculating a volume of a biogenic gas in a hydrocarbon extraction process.

FIG. 3 is a process flow diagram showing a method 300 for producing hydrocarbons in accordance with an exemplary embodiment of the present invention. Analytical measurements may be taken of sediments that host microbial gas generation to determine such thermodynamic conditions such as the concentrations of $CO_2$, $H_2$ and $CH_4$ as shown at block 302. At block 304, a plurality of environmental and/or biological characteristics are determined and input into the model. These inputs include the concentrations of the acceptors, $CO_2$, and of the donors, such as $H_2$, but also may include $HCO_3^-$. Inputs further include information regarding the pore-water chemistry and levels of $Na^+$, $Cl^-$, pH, and $HCO_3^-$, and temperature. Biological inputs may include the biomass, ATPs synthesized and energy required for ATP synthesis. These inputs can be variable over time, temperatures, pressures, and geochemical conditions. At block 306, the model is run for the time period of interest. The model will terminate if the reaction becomes energetically unfavorable to continue methanogenesis or the time window has reached its end. At block 308, a series of methanogenic rates are calculated at the conditions for each time step and temperature of interest. At block 310, the series of methanogenic rates calculated at each time step may be used to calculate a volume of biogenic gas in the area of interest. Hydrocarbons may be extracted from the area of interest using the predicted biogenic gas generation, as shown at block 312.

The environmental characteristics, e.g., hydrogen concentration, carbon dioxide concentration, pore-water chemistry, temperature, pressure, can be estimated for an area of interest or may be measured. For example, the temperature may be directly measured or may be estimated based on the depth of the area of interest. For example, the pressure may be directly measured or may be estimated based on the depth of the area of interest. For example, the hydrogen concentration, carbon dioxide concentration, and/or pore-water chemistry and associated qualities, such as level of Na+, Cl−, $HCO_3^-$, and/or pH of the area of interest may be measured from samples obtained from the area of interest. For example, the samples may include water column samples, rock samples, sediment samples, and/or rock and sediment samples that include pore-water. For example, sediment samples may come from small sediments coops, push cores, box cores, gravity cores, piston cores, or jumbo piston cores. If the samples are not being analyzed immediately, the samples may be frozen as soon as possible after collection to preserve the integrity of the sample. That is, the sediment, water, and/or rock samples may be frozen as soon after collection as possible to prevent changes within the samples due to the sample being maintained at a different conditions than those at which the sample were collected. For example, the samples may be maintained at a low temperature, such as less than −60° C., or less than −70° C., or less than −80° C., until analyses are performed. In some embodiments, the sample may be maintained at a temperature in the range of −60° C. to −100° C., or from −60° C. to −80° C., until analyses are performed. The obtained samples may be analyzed by chemical analyses to determine one or more environmental characteristics such as hydrogen concentration, carbon dioxide concentration, pore-water chemistry. Chemical analysis to determine pore-water concentration may comprise determining one or more of sodium concentration, chlorine concentration, bicarbonate concentration, and/or the pH of the sample.

Figure 4:
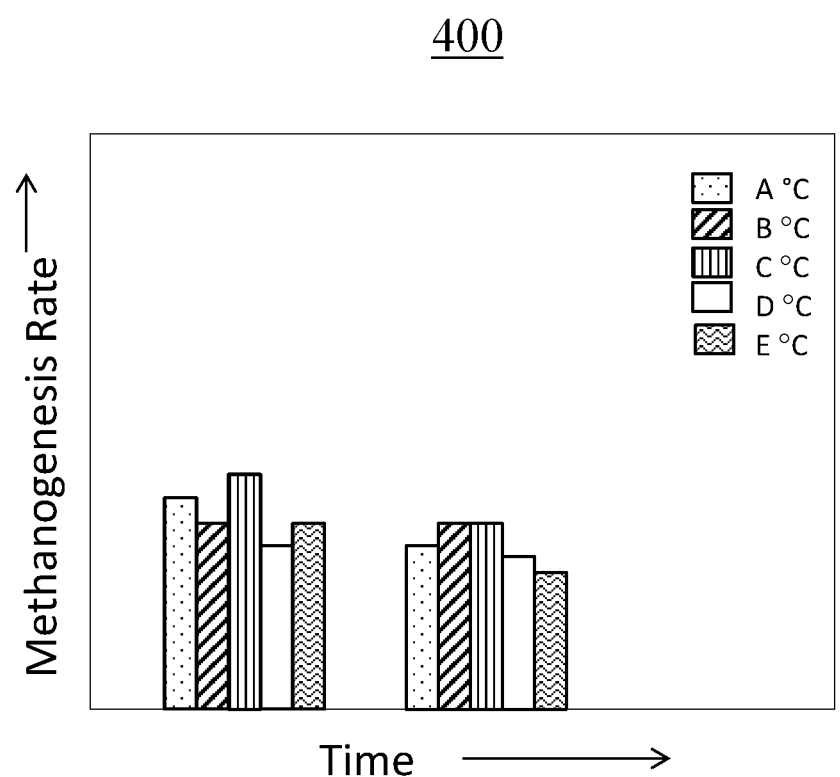
FIG. 4 is an example of an output for methods of the present techniques illustrating the rate of methanogenesis over time.

FIG. 4 illustrates an example of an output 400. As seen in FIG. 4, the methanogenesis rate can be calculated at different periods of time for different temperatures. These results are the methanogenesis rates for the given geochemical and biological conditions for the area and period of time of interest. Thus for example, the model can be used to determine the methanogenesis rate (e.g., mmol/ft³/year) at a first time period, e.g., 100,000 years, at five different temperature conditions (e.g., temperatures A, B, C, D, and E in FIG. 4). The model can then be used to determine the methanogenesis rate at a second time period, e.g., 1,000,000 years, at the same temperature conditions.

The methods described herein can be utilized to predict a volume of biogenic gas in an area of interest. The methods can further be used to predict a volume of biogenic gas in the area of interest for a specific time of interest, or for different times of interest. The predicted volumes can then be used to refine a hydrocarbon exploration, development, or production strategy. For example, the information can be used to determine evaluate the prospects of the area of interest, and to enhance subsequent ranking of a prospect. The information can be used to refine or develop hydrocarbon exploration, development, and production strategies by identifying areas of interest that have larger volumes of hydrocarbons. Ultimately, this information can be used to produce hydrocarbons from the subsurface accumulation.

Additionally, the methods described herein can be integrated with other basin-modeling techniques. For example, the methods can be integrated with time-temperature histories for the area of interest, and the time-temperature history can be used to vary the temperature within the area of interest over time so that the methods described herein can be used to predict how the volume of biogenic gas in the area of interest changed over time.

An alternative embodiment of this invention would be the application in other settings such as secondary gas generation from oil biodegradation or under conditions that have different $H_2$ concentrations—e.g. hydrothermal systems.

The results of the methods proposed herein were compared to an extensive list of published methanogenesis rates from multiple global locations. The rates determined using the methods described herein and the rates using published models are the same order of magnitude, e.g. mol/km3/day. This consistency validates the approach of the methods described herein to capturing the geochemical and biological conditions under methanogenic conditions.

Figure 5:
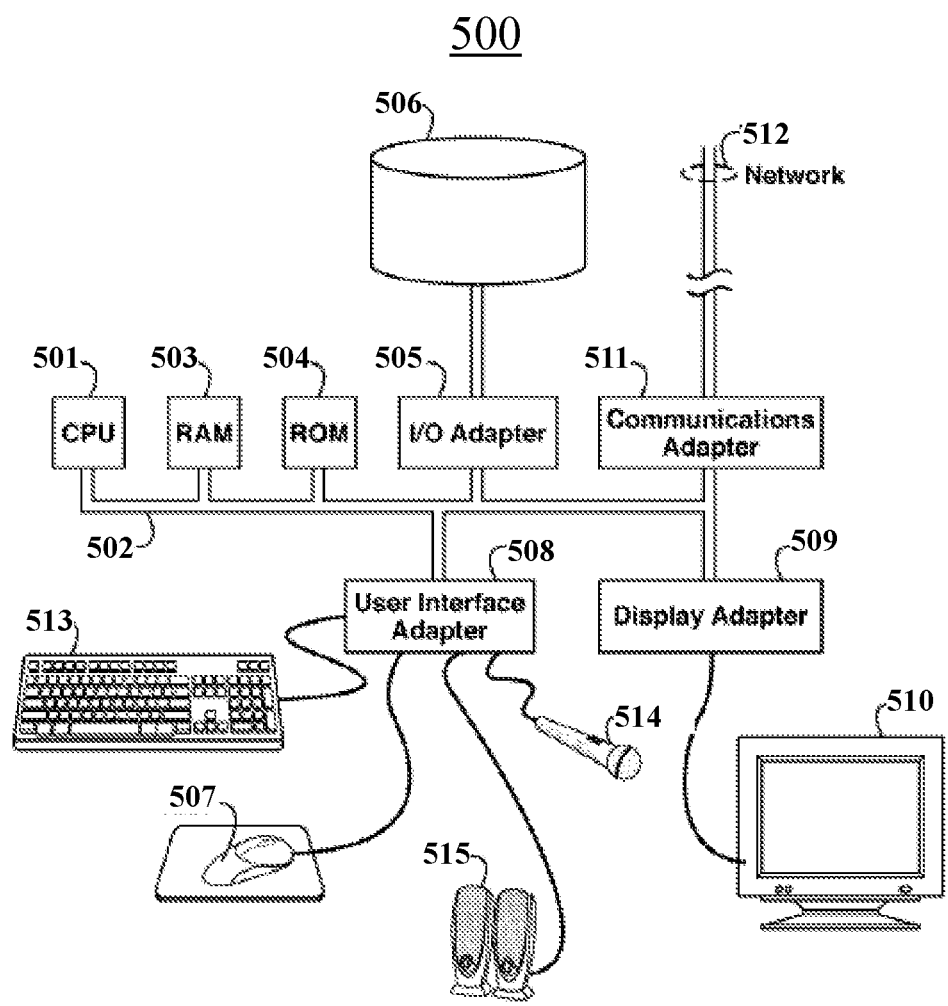
FIG. 5 is a block a diagram of a computer system that may be used in exemplary embodiments of the present techniques.

FIG. 5 is a block diagram of a computer system 500 in accordance with an exemplary embodiment of the present techniques. A central processing unit (CPU) 501 is coupled to system bus 502. The CPU 501 may be any general-purpose CPU, although other types of architectures of CPU 501 (or other components of exemplary system 500) may be used as long as CPU 501 (and other components of system 500) supports the inventive operations as described herein. The CPU 501 may execute the various logical instructions according to various exemplary embodiments. For example, the CPU 501 may execute machine-level instructions for performing processing according to the operational flow described above.

The computer system 500 may also include computer components such as a random access memory (RAM) 503, which may be SRAM, DRAM, SDRAM, or the like. The computer system 500 may also include read-only memory (ROM) 504, which may be PROM, EPROM, EEPROM, or the like. RAM 503 and ROM 504 hold user and system data and programs, as is known in the art. The computer system 500 may also include an input/output (I/O) adapter 505, a communications adapter 511, a user interface adapter 508, and a display adapter 509. The I/O adapter 505, the user interface adapter 508, and/or communications adapter 511 may, in certain embodiments, enable a user to interact with computer system 500 in order to input information.

The I/O adapter 505 preferably connects a storage device(s) 506, such as one or more of hard drive, compact disc (CD) drive, floppy disk drive, tape drive, etc. to computer system 500. The storage device(s) may be used when RAM 503 is insufficient for the memory requirements associated with storing data for operations of embodiments of the present techniques. The data storage of the computer system 500 may be used for storing information and/or other data used or generated as disclosed herein. The communications adapter 511 may couple the computer system 500 to a network (512), which may enable information to be input to and/or output from system 500 via the network (for example, the Internet or other wide-area network, a local-area network, a public or private switched telephony network, a wireless network, any combination of the foregoing). User interface adapter 508 couples user input devices, such as a keyboard 513, a pointing device 507, speaker 515, a microphone 514, and the like, to computer system 500. The display adapter 509 is driven by the CPU 501 to control, the display on a display device 510. Information and/or representations pertaining to a portion of a hydrocarbon extraction process or a hydrocarbon extraction simulation, such as displaying data corresponding to a physical or financial property of interest, may thereby be displayed, according to certain exemplary embodiments.

The architecture of system 500 may be varied as desired. For example, any suitable processor-based device may be used, including without limitation personal computers, laptop computers, computer workstations, and multi-processor servers. Moreover, embodiments may be implemented on application specific integrated circuits (ASICs) or very large scale integrated (VLSI) circuits. In fact, persons of ordinary skill in the art may use any number of suitable structures capable of executing logical operations according to the embodiments.

For example, the system 500 may be a computer system utilized in a hydrocarbon extraction process. The system may include a processor; memory in communication with the processor; and a set of instructions stored in memory and accessible by the processor. The system may be configured to display the methanogenesis rates for the various time steps and/or the volume data from one or more of the time steps. The set of instructions, when executed by the processor, are configured to identifying a plurality of environmental characteristics for one or more periods of time for the area of interest; determining a methanogenesis rate for the one or more periods of time for the area of interest, wherein the methanogenesis rate is determined by the environmental characteristics and integrating a function indicating the hydrogen activity for the period of time in the area of interest, a function indicating the carbon dioxide activity for the period of time in the area of interest, and a function indicating the microbial respiration energy ($R_e$) for the period of time in the area of interest; and predicting the volume of the biogenic gas based on the methanogenesis rate for the one or more of the periods of time for the area of interest.

In view of the many possible embodiments to which the principles of the disclosed invention may be applied, it should be recognized that the illustrative embodiments are only preferred examples of the invention and should not be taken as limiting the scope of the invention.

What is claimed is:

1. A method for predicting a volume of biogenic gas for an area of interest, the method comprising:
   (a) obtaining a sample from the area of interest and analyzing the sample via a chemical analysis to identify a plurality of environmental characteristics, wherein the plurality of environmental characteristics comprise at least a hydrogen concentration and a carbon dioxide concentration;
   (b) determining a methanogenesis rate for one or more periods of time for the area of interest using the following equation:

Rate=$k*M*D*A*R_e$ wherein k is a rate constant;
   wherein M is a biomass;
   wherein D is a function indicating the hydrogen activity for the one or more periods of time in the area of interest;
   wherein A is a function indicating the carbon dioxide activity for the one or more periods of time in the area of interest, and
   wherein $R_e$ is a thermodynamic function indicating the microbial respiration energy ($R_e$) for the one or more periods of time in the area of interest;
   (c) predicting the volume of the biogenic gas based on the methanogenesis rate for the one or more periods of time for the area of interest; and
   (d) extracting hydrocarbons from the area of interest using the predicted volume of biogenic gas.

2. The method of claim 1, wherein the sample comprises at least one of a water sample, a rock sample, a sediment sample, a core sample, or combinations thereof.

3. The method of claim 1, wherein the environmental characteristics include a pore-water chemistry.

4. The method of claim 3, wherein the pore-water chemistry comprises the concentration of sodium.

5. The method of claim 3, wherein the pore-water chemistry comprises the concentration of chlorine.

6. The method of claim 3, wherein the pore-water chemistry comprises the concentration of bicarbonate.

7. The method of claim 3, wherein the pore-water chemistry comprises the pH.

8. The method of claim 1, wherein the energy available for microbial activity further comprises the calculation of the free energy change of microbial respiration.

9. The method of claim 8, wherein the calculation of the free energy change of microbial respiration includes the numbers of ATPs synthesized.

10. The method of claim 1, wherein D is determined by the following equation:

$$D = \frac{H_2}{K_D + H_2}$$

where $H_2$ is the concentration of $H_2$; and
where $K_D$ is the $H_2$ concentration at which the specific growth rate of the microbial community or organism is one-half of its maximum.

11. The method of claim 1, wherein A is determined by the following equation:

$$A = \frac{CO_2}{K_A + CO_2}$$

where $CO_2$ is the concentration of $CO_2$; and
where $K_A$ is the $CO_2$ concentration at which the specific growth rate of the microbial community or organism is one-half of its maximum.

12. The method of claim 1, wherein the microbial respiration energy function $R_e$ is determined by the following equation:

$$R_e = 1 - e^{\frac{\Delta G_{redox} - m\Delta G_{atp}}{XRT}}$$

where $\Delta G_{redox} - m\Delta G_{atp}$ is the free energy change of microbial respiration;
where m is the number of ATPs synthesized;
where X is the average stoichiometric number of reaction;
where R is the universal gas constant; and
where T is the temperature.

13. The method of claim 1, wherein the microbial respiration energy function $R_e$ is determined by the following equation:

$$Re = (1 - (Q/K)^{\omega}) * \exp^{((-\omega * natp * \Delta Gatp)/(RT))\Omega})$$

where Q is the reaction quotient;
where K is the equilibrium constant for the reaction;
where $\omega$ and $\Omega$ are reaction orders which prevent the reaction from proceeding under conditions that inhibit microbial methanogenesis; and where natp*ΔGatp are collectively a term that combines the number of ATP (natp) generated and the free energy required to sustain the microbial activity and generation of methane.

\* \* \* \* \*